United States Patent [19]

Meador et al.

[11] Patent Number: 5,547,862
[45] Date of Patent: Aug. 20, 1996

[54] VECTORS CONTAINING MULTIPLE PROMOTERS IN THE SAME ORIENTATION

[75] Inventors: James Meador; Hoyt E. McElroy; Michelle L. Herrmann; Matthew Winkler, all of Austin, Tex.

[73] Assignee: Ambion Inc., Austin, Tex.

[21] Appl. No.: 99,867

[22] Filed: Jul. 29, 1993

[51] Int. Cl.$^6$ .......................... C12N 15/11; C12N 15/70; C12P 19/34
[52] U.S. Cl. ...................... 435/91.3; 435/320.1; 536/24.1
[58] Field of Search ............................... 435/91.3, 320.1; 536/24.1

[56] References Cited

U.S. PATENT DOCUMENTS 4,766,072   8/1988   Jendrisak et al. ...................... 435/91.3

OTHER PUBLICATIONS

Stratagene 1993 Product Catalog, Stratagene Cloning Systems, p. 26.
Brosius, DNA 8(10): 759–777 (1989).
Alting–Mees et al. (1992), Strategies in Molecular Biology 5: 58–61.
M. A. Alting–Mees, et al., "pBluescript II: gene mapping vectors", *Nucleic Acids Research*, vol. 17, No. 22, p. 9494 (1989).
Jürgen Brosius, "Compilation of Superlinker Vectors", *Methods in Enzymology*, vol. 216, pp. 469–483 (1992).
Jeanne E. Brown et al., "Sequences of three promoters for the bacteriophage SP 6 RNA polymerase", *Nucleic Acids Research*, vol. 14, No. 8, pp. 3521–3526 (1986).
Eugene T. Butler et al., "Bacteriophage SP6–specific RNA Polymerase", *J. of Bio. Chemistry*, vol. 257, No. 10, pp. 5772–5778 (1982).
John J. Dunn et al., "Complete Nucleotide Sequence of Bacteriophage T7 DNA and the Locations of T7 Genetic Elements", *J. Mol. Biol.*, vol. 166, pp. 477–535 (1983).
M. Ernoult–Lange et al., "Simian Virus 40 Late Promoter Region Able to Initiate Simian Virus 40 Early Gene Transcription in the Absence of the Simian Virus 40 Origin Sequence", *J. of Virology*, vol. 50, No. 1, pp. 163–173 (1984).
Michel Heusterspreute et al., "Vectors with restriction site banks IV. pJRD184, a 3793–bp plasmid vector having 43 unique cloning sites", vol. 39, pp. 299–304 (1985).
John F. Klement et al., "Distrimination Between Bacteriophage T3 and T7 Promoters by the T3 and T7 RNA Polymerases Depends Primarily upon a Three Base–pair Region Located 10 to 12 Base–pairs Upstream from the Start Site", *J. Mol. Biol.*, vol. 215, pp. 21–29 (1990).
Craig T. Martin et al., "Kinetic Analysis of T7 RNA Polymerase–Promoter Interactions with Small Synthetic Promoters", vol. 26, pp. 2690–2696 (1987).
D. A. Melton et al., "Efficient in vitro synthesis of biologically active RNA and RNA hybridization probes from plasmids containing a bacteriophage SP6 promoter", *Nucleic Acids Research*, vol. 12, No. 18, pp. 7035–7056 (1984).
Claire E. Morris et al., "Cloning and expression of the bacteriophage T3 RNA polymerase gene", *Gene*, vol. 41, pp. 193–200 (1986).
Dola Sengupta et al., "Relative Efficiency of Utilization of Promoter and Termination Sites by Bacteriophage T3 RNA Polymerase", *J. of Bio. Chem.*, vol. 264, No. 24, pp. 14246–14255 (1989).
Stanley Tabor et al., "A bacteriophage T7 RNA polymerase/promoter system for controlled exclusive expression of specific genes", *Proc. Natl. Acad. Sci. USA*, vol. 82, pp. 1074–1078 (1985).
W. Zillig et al., "RNA polymerases and transcription in archaebacteria", *Biochem Soc. Symp.*, vol. 58, pp. 79–88 (Printed in Great Britain) (1990).

*Primary Examiner*—Mindy Fleisher
*Assistant Examiner*—Philip W. Carter
*Attorney, Agent, or Firm*—Arnold, White & Durkee

[57] ABSTRACT

Disclosed are novel DNA segments, vectors and plasmids containing multiple promoters for use with various polymerases in order to transcribe cloned DNA into RNA. A preferred vector, termed pTRIPLEscript™, is described which contains the SP6, T7, and T3 phage promoters in the same orientation and on the same side of a multiple cloning site. This vector efficiently synthesizes in vitro transcripts from all three promoters under conditions of both limiting and saturating nucleotide concentrations. This vector also promotes transcription without crosstalk, i.e., without nonspecific initiation at inappropriate promoters.

26 Claims, 5 Drawing Sheets

VECTORS CONTAINING MULTIPLE PROMOTERS IN THE SAME ORIENTATION

BACKGROUND OF THE INVENTION

1. Field of the Invention

The present invention relates generally to the field of molecular biology and to cloning vectors. Particularly disclosed are novel DNA segments, vectors and plasmids containing multiple distinct promoters in the same orientation which allow a single vector to be employed in connection with distinct polymerases to efficiently generate RNA transcripts.

2. Description of the Related Art

In vitro synthesized RNA is an important reagent in many molecular biological techniques. In vitro transcription is used, to synthesize radioactively- or non-isotopically-labeled probes for Northern and Southern blotting, in situ hybridization and ribonuclease protection assays, which are all important tools for use in both research and clinical diagnostic embodiments. In vitro transcription is also used to synthesize unlabeled synthetic mRNAs for use, for example, in microinjection studies, antisense technology and in vitro translation.

The DNA template for in vitro transcription reactions is typically plasmid DNA which contains an SP6, T7, or T3 phage promoter upstream from the sequence to be transcribed. Many modern multipurpose cloning vectors contain two phage polymerase promoters in opposite orientations flanking the multiple cloning site (Jendriask et al., U.S. Pat. No. 4,766,072). These "dual opposable promoter" vectors allow both sense and antisense transcripts to be made from the same plasmid and are widely used in molecular biology.

Although various cloning vectors containing phage promoters are currently available, they all suffer from certain drawbacks. For example, in most plasmid vectors transcription proceeds in one direction from a single promoter. When two promoters are present, such as SP6 and T7, they are generally utilized so that transcription from one promoter proceeds towards the other, i.e., they function as opposed, not uni-directional, promoters and stimulate transcription of alternate strands of the DNA insert.

There are at least two situations in which it would be useful to have two, three or more promoters in the same orientation and on the same side of a multiple cloning site. The first is where a clone is being distributed to many different laboratories, as is often necessary for swift scientific progress. In these cases it would be a great labor-saving device to be able to transcribe the clone with different polymerases, such as any of the three commonly used phage polymerases, without the necessity for prior subcloning.

Secondly, and perhaps more importantly, it is not uncommon to encounter sequences which do not transcribe well with a particular polymerase. This may be due to the inadvertent presence of sequences which mimic polymerase termination signals or other unknown causes. This can be a particular problem when synthesizing high specific activity radiolabeled RNA probes where one nucleotide is present at limiting concentrations. Such poor transcription can often be alleviated by transcribing with a different polymerase. The ability to employ a second or third polymerase without having to subclone into a new plasmid would be a major advantage.

SUMMARY OF THE INVENTION

The present invention seeks to overcome these and other drawbacks inherent in the prior art by providing novel DNA segments, vectors and plasmids which contain multiple promoters in the same orientation. This allows a single vector to be employed in connection with various polymerases to efficiently generate RNA transcripts. The vectors of the invention may be employed to synthesize both high specific activity probes and unlabeled mRNA transcripts with little or no crosstalk between the promoters.

Accordingly, the invention concerns recombinant vectors for use in synthesizing RNA which comprise multiple, i.e., at least two, distinct promoters in the same orientation. This may also be described as comprising promoters in tandem. "In tandem" does not refer to the presence of only two promoters or dual promoters, rather, it means any number of promoters which are in the same orientation and are capable of stimulating transcription in the same direction. Promoters in tandem will therefore be on the same side of at least one multiple cloning site, such as a first or major multiple cloning site, so that they are capable of stimulating the transcription of a DNA segment inserted into that site, i.e., inserted functionally downstream of the promoter.

In certain aspects, the invention concerns recombinant vectors for use in synthesizing RNA which comprise a cloning site, capable of accepting an RNA transcription unit or units, which cloning site is positioned downstream of a promoter region which includes multiple, i.e., at least two, promoters recognized by distinct RNA polymerases. The promoters will naturally be positioned so as to promote expression from any RNA transcription units, i.e., inserted exogenous DNA, which may be inserted into the cloning site.

"Multiple" and "distinct", in the context of "multiple distinct promoters" mean at least two promoters recognized by distinct RNA polymerases. Multiple therefore refers to more than one promoter, such as two, three, four or more promoters up to and including about 10 or 15 promoters. There is generally no upper limit on the number of promoters which may be used in accordance with the present invention. Choosing the number of promoters for use in given vector will generally be dictated by a combination of functional and physical parameters of the vector and its construction. For instance, the number of steps required for vector construction may be weighed against the ultimate uses for which it is intended, e.g., the number of distinct laboratories it may be used in and the number of host cells it may be propagated in and the like.

Vectors intended for broader distribution and/or use may contain larger numbers of promoters and their utility will generally warrant any extra steps required for their synthesis. However, in most practical terms, the number of promoters which one would desire to use for a functional vector will generally be less than about 10, and mostly be less than 5, with vectors having four promoters being preferred and those having three promoters being most preferred. Recombinant vectors comprising two distinct promoters in the same orientation are also contemplated for use in certain embodiments, such as directly comparing the effectiveness of specific gene transcription from two promoters.

Any two or more of a variety of promoters may be employed in vectors and plasmids of the present invention so long as there is an RNA polymerase enzyme available to stimulate transcription from the promoter. In preferred embodiments, the RNA polymerase will be specific for a particular promoter and the enzyme will be available in a partially or substantially purified state or in an essentially homogenous preparation. By their nature, most RNA polymerases are "specific" for their particular promoter, i.e., they have a high preference for their promoter sequence, or motif, and do not stimulate significant transcription from other promoters. Thus, specificity will not generally be a problem.

For an RNA polymerase enzyme to be partially purified means that it be purified free from other natural components so that it functions effectively in in vitro transcription reactions. This means that it is free from agents which may substantially inhibit or interfere with its activity and that it is available in amounts effective to promote transcription when added to an appropriate reaction mixture. RNA polymerase enzymes may be purified by any of the various methods described in the scientific literature or may be obtained in essentially homogenous preparations from commercial sources.

The promoters used may be from any source, including bacterial, viral, phage and eukaryotic, including plant and animal, promoters. The following lists are, of course, intended to be exemplary and not exhaustive. Bacterial promoters include promoters from *E. coli*, *S. typhimurium* and *B. subtilis*. Viral promoters include the SV40 late promoter from simian virus 40, the Baculovirus polyhedron enhancer/promoter element, Herpes Simplex Virus thymidine kinase (HSV tk), the 35S promoter from Cauliflower Mosaic Virus (CMV) and various retroviral promoters. Suitable phage promoters include, but are not limited to the *E. coli* T7 and T3 phage promoters, the *S. typhimurium* phage SP6 promoter, *B. subtilis* SP01 phage and *B. subtilis* phage phi 29 promoters, and N4 phage and K11 phage promoters. Plant and animal promoters may include promoter sequences from significantly expressed genes such as the α-tubulin gene and various zein genes in plants and immunoglobulin and hormone genes in animals.

Recombinant shuttle vectors with multiple promoters also form another aspect of the invention. "Shuttle vectors" are those which can be propagated in both procaryotic and eukaryotic host cells, e.g., in both *E. coli* cells and either yeast or mammalian cells. Shuttle vectors in accordance with the present invention are distinct from those in present use as they will comprise at least two promoters capable of stimulating transcription in procaryotic host cells, such as bacterial or phage promoters, in combination with one or more eukaryotic or viral promoters capable of stimulating transcription in eukaryotic cells, such as yeast, CHO cells or COS cells. These vectors may also be functionally described as vectors comprising in tandem promoters for in vitro transcription, e.g., phage promoters, and promoters for in cellulo or in vivo transcription. One example of a preferred shuttle vector is a vector comprising the three commonly-used phage promoters, SP6, T7 and T3, in addition to the SV40 promoter.

In certain embodiments, the use of phage promoters and their respective polymerases is preferred. The phage promoters SP6, T7 and T3 are particularly preferred as they are most generally used in the art. The preferred sequences for use as SP6, T7 and T3 promoters are nucleotides 4–23, nucleotides 34–56 and nucleotides 63–82, respectively (each of which sequences are present within SEQ ID NO:2, as marked on FIG. 1A). The SP6, T7 and T3 RNA polymerases, from the *S. typhimurium* phage SP6 and the *E. coli* phages T7 and T3, respectively, are readily available, for example, from commercial sources such as Promega, Pharmacia and Ambion, or by preparation according to the protocols of Tabor et al. (1985), Morris et al. (1986), and Butler et al., (1982), each incorporated herein by reference. The most preferred promoter regions will be those which include a nucleotide sequence in accordance with the nucleotide sequence set forth by residues 1–79 of SEQ ID NO:1 or the complement thereof.

Vectors in accordance with the present invention may include two of the most preferred phage promoters alone, i.e., SP6 and T7, SP6 and T3, or T7 and T3, or may variously include two such promoters with an additional phage promoters, e.g., T7, K11, and SP6, all three of the SP6, T7 and T3 promoters, or all three promoters in combination with other promoter elements such as the SV40 promoter or the Baculovirus polyhedron enhancer/promoter.

The recombinant vectors and plasmids of the invention will comprise at least one cloning site capable of accepting an RNA transcription unit. "A cloning site" is a DNA sequence which includes at least one restriction enzyme site into which the exogenous DNA to be transcribed will be inserted. The term "exogenous DNA" is used in the same manner as "RNA transcription unit", and both of these terms refer to a DNA segment, segments or transgene(s) which are inserted into one of the vectors of the invention in order to obtain an RNA copy. An RNA transcription unit is, therefore, DNA which is to be transcribed and is not DNA containing the promoter sequences themselves.

Restriction enzyme sites are short sequences of DNA which are specifically recognized by a given restriction enzyme which cuts DNA with that specific sequence. Restriction enzymes are typically used in the art to cut DNA and insert exogenous DNA into the site, which is then re-sealed or ligated to form a recombinant DNA sequence or construct (Sambrook et al., 1989).

There is no limit to the number of such restriction sites present within the vector so long as there is at least one, for example, there may be two, three, five, ten, twenty, thirty or more. In preferred embodiments, the vectors of the invention will contain a stretch of DNA with multiple restriction enzyme cleavage sites, this is termed "a multiple cloning site". This will allow greater scope in the manipulation of DNA sequences so that a variety of DNA segments may be straightforwardly inserted into the vector. The most preferred multiple cloning sites will be those which include a nucleotide sequence in accordance with the nucleotide sequence set forth by residues 80–150 of SEQ ID NO:1 or the complement thereof.

However, the invention is not limited to one specific multiple cloning site and any particular one may be used. Many restriction site sequences and multiple cloning sites are known to those of skill in the art and the corresponding restriction enzymes are available commercially from many sources. The number and type of such restriction sites in any vector may be varied almost without limit and additional ones created to allow the insertion of any piece of DNA. Commercial constructs which may be employed as starting points for constructing a novel multiple promoter plasmid include, for example, Bluescript and superlinker vectors (Heusterspreute et al., 1985; Brosius, 1992; Alting-Mecs & Short, 1989, each incorporated herein by reference).

Restriction sites may also be present between individual promoters in the vector, allowing distinct DNA segments or genes to be inserted between one or more of the promoters. Using these types of construct would allow one RNA polymerase to stimulate the transcription of just one of the genes or sequences. Depending on the particular construction employed, using a distinct polymerase may result in the transcription of a distinct sequence or the transcription of a single transcript containing two or more sequences, i.e., a polytranscript.

In one embodiment, the invention provides recombinant vectors for use in synthesizing RNA which comprise at least two distinct and substantially adjacent promoters recognized by distinct RNA polymerases, which are positioned upstream of a cloning site capable of accepting an RNA transcription unit, wherein the unit would be under the control of the promoters. "Substantially adjacent" in this context means not separated by large stretches of intervening DNA sequences, and generally located within about 25 or about 15 bases, and most preferably, located within about 10 or even 5 bases. Particularly preferred vectors may include a nucleotide sequence in accordance with the nucleotide sequence set forth by residues 1–150 of SEQ ID NO:1 or the complement thereof.

The vectors of the invention may be in the form of plasmids or even cosmids or other DNA constructs. In some instances, the term "recombinant vector" means a DNA molecule which is propagated in host cells, for example, in E. coli. However, in its broadest sense, "recombinant vector" means any DNA segment which is designed by man for use in certain techniques and which does not occur in that particular form in nature. Therefore, in this sense, a recombinant vector may also be a linear piece of DNA.

Accordingly, this invention also concerns DNA segments for use in synthesizing RNA which comprise a cloning site capable of accepting an RNA transcription unit, wherein the cloning site is positioned downstream of a promoter region which includes at least two promoters which are recognized by distinct RNA polymerases and are capable of promoting expression of the RNA transcription unit. Such linear constructs or DNA segments may be made by techniques which do not include bacterial passage, for example, by using the widely available Polymerase Chain Reaction (PCR), as will be known to those of skill in the art in light of the present disclosure.

In certain preferred embodiments, the vectors will be in the form of recombinant circular plasmids. The most functionally useful plasmids will be those that are substantially pure, i.e., are purified free from other components, such as DNA constructs and non-plasmid DNA, so that it functions effectively in in vitro transcription reactions. Suitable methods for plasmid preparation and purification will be known to those of skill in the art in light of the present disclosure.

Accordingly, the invention also provides recombinant plasmids in circular form for use synthesizing RNA which comprise a promoter region which has three substantially adjacent phage promoters, preferably, SP6, T7 and T3 promoters, each recognized by a distinct phage-encoded RNA polymerase, positioned upstream of and closely adjacent to a multiple cloning site capable of accepting an RNA transcription unit, wherein such a unit would be under the transcriptional control of the phage promoters.

The preferred plasmids will generally include a DNA sequence in accordance with SEQ ID NO:1 or SEQ ID NO:2. The most preferred vector disclosed herein is the triple phage promoter plasmid termed pTRIPLEscript™ which contains the SP6, T7, and T3 phage promoters in tandem along with a multiple cloning site.

The invention also encompasses the recombinant vectors and plasmids in which an RNA transcription unit or exogenous DNA segment has been inserted into the cloning site, so as to fall under the transcriptional control of the promoters, and methods of using such constructs to prepare RNA. Recombinant host cells which include multiple promoter vectors with or without recombinant transcription units, such as host cells in which the vectors are being propagated, also form another aspect of the invention.

In still further embodiments, the present invention concerns methods for preparing RNA transcripts from DNA sequences. The methods of the invention generally comprise preparing a recombinant vector comprising a promoter region which includes at least two promoters recognized by distinct RNA polymerases, as described above, inserting a DNA sequence downstream of the promoters, and utilizing the vector in an in vitro transcription protocol.

The act of utilizing the vector in an in vitro transcription protocol generally involves contacting the vector containing the inserted DNA with a reaction mixture including an RNA polymerase capable of functionally interacting with one of said promoters under conditions effective to allow transcription to proceed. Naturally, the reaction mixture will contain other essential elements, such as appropriate concentrations of the four nucleotides, and the reaction will be conducted in an appropriate manner using suitable buffers, appropriate temperatures, and the like.

In vitro transcription is now routine in the art, as exemplified by U.S. Pat. No. 4,766,072, incorporated herein by reference. As will be known to the skilled artisan, where the vector containing the inserted DNA is in the form of a circular plasmid vector, the plasmid should first be linearized, for example, by cutting with a restriction enzyme, prior to contact with the reaction mixture.

It is contemplated that particularly advantageous methods for preparing RNA are those which use vectors comprising phage promoters in combination with reaction mixtures which include phage-encoded RNA polymerases. In certain embodiments, the use of a vector comprising three distinct promoters, and more preferably, the three phage promoters SP6, T7 and T3, is preferred, with the plasmid pTRIPLEscript™ being particularly preferred.

The vectors of the invention, as exemplified by the pTRIPLEscript™ plasmid, may be used to synthesize RNA transcripts using various reaction mixtures. For example, labeled nucleotides may be employed to generate a labelled RNA product. In these case, the reaction mixture would generally include subsaturating or limiting nucleotide concentrations, to provide high specific activity probes. Alternatively, reaction mixtures including saturating nucleotide concentrations may be employed to generate unlabeled 'synthetic mRNA'.

There is effectively no limit to the type of DNA insert, segment, or transgene which may be transcribed into RNA as described herein. Both coding and non-coding DNA may be used to generate RNA species, for use, e.g., as probes in various molecular biological embodiments including cloning and diagnostic studies. The DNA may also be used to generate RNA for subsequent translation into one or more proteins, polypeptides, peptides, antigens and the like. In certain embodiments, a single recombinant insert may be used which includes distinct coding sequences. Also, one or more DNA segments may be inserted between various promoters, i.e., functionally downstream of one promoter and before another, so that different polymerases promote transcription of different RNA species, including both single and polytranscripts. Antisense RNA may also be produced for use inhibiting gene transcription or translation.

BRIEF DESCRIPTION OF THE DRAWINGS

FIG. 1. Plasmid pTRIPLEscript™ and new sequence therein. FIG. 1 consists of FIG. 1A and FIG. 1B.

FIG. 3. Transcription of pTRIPLEscript using limiting nucleotide vs. saturating nucleotide and polymerase conditions. FIG. 3 consists of FIG. 3A and FIG. 3B. All transcription reactions were done with 0.5 μg of pTRIPLEscript containing a 589 bp rabbit β-globin insert. Lanes 1, 4, and 8 are the RNA molecular mass markers as in FIG. 2. Lanes 2, 3, and 4 are reactions using 10 units of SP6, T7, and T3 RNA polymerase, respectively, and limiting UTP concentrations, 13 μM. Lanes 6, 7, and 8 are reactions using 80 units of SP6, T7, and T3 RNA polymerase, respectively, and saturating UTP concentrations, 500 μM.

DETAILED DESCRIPTION OF THE PREFERRED EMBODIMENTS

Promoters are DNA sequence elements that control the transcription of genes, i.e., protein-encoding DNA sequences. In nature, genes are composed of multiple genetic elements which allow for their fine control, promoters are one of these such elements, enhancers, silencers, and termination and polyadenylation signals are just a few examples of others. The cellular machinery is able to gather and integrate the regulatory information conveyed by each element, allowing different genes to evolve distinct patterns of transcriptional regulation.

In the most general sense, a promoter may be described as a transcriptional control module that is clustered around the site for RNA polymerase binding. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–25 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Promoters may be used by man in a variety of different molecular biological embodiments. For example, the production of RNA from cloned DNA in vitro is now a routine procedure in molecular biology. The systems for achieving this generally use plasmids containing bacteriophage promoters and corresponding purified DNA-dependent RNA polymerases, as obtainable from phage-infected cells. Typically-used promoters are the late promoter from the *Salmonella typhimurium* bacteriophage SP6 and promoters from the *E. coli* bacteriophages T7 and T3. These promoters are incorporated into vector constructs adjacent to several unique restriction enzyme sites, i.e., a multiple cloning site, so that a variety of DNA sequences may be inserted into that region.

After construction, the purified plasmid is linearized by cutting with a restriction enzyme (e.g., Sambrook et al., 1989, incorporated herein by reference). Then a reaction mixture containing the four nucleotide triphosphate substrates and the appropriate RNA polymerase is added which, generally, results in the synthesis of large amounts of RNA. The RNA polymerase enzymes used in such processes are fairly specific and largely only recognize their own phage promoters. Transcription reactions using either promoter system are mostly very efficient and many copies of full length RNA may be produced from each template molecule. It is thus possible to synthesize milligram amounts of RNA from any cloned DNA sequence, which may then be used in a variety of embodiments.

Vectors which contain two phage polymerase promoters in opposite orientations flanking a multiple cloning site have been described (Jendriask et al., U.S. Pat. No. 4,766,072). These vectors allow both sense and antisense transcripts to be made from the same plasmid. Despite advances such as these, there remain certain limitations in this technology. For example, in these vectors, the SP6 and T7 promoters function as opposed, not uni-directional, promoters and stimulate transcription of alternate strands of the DNA insert.

The present inventors reasoned that there are situations in which it would be useful to have in vitro transcription vectors with two, three or more promoters in the same orientation and on the same side of a multiple cloning site. They therefore designed and constructed such DNA segments vectors and plasmids, which have distinct advantages over those currently employed in the art. These include, for example, the ease of distributing functional plasmids to various laboratories for immediate use without sub-cloning, and also, the ability to overcome the unexplained low-level transcription which sometimes occurs with a given construct without further sub-cloning. In light of the present disclosure, it will be understood that a wide range of multiple-promoter constructs and plasmids fall within the scope of the present invention.

A variety of promoters may be employed in connection with the present invention so long as there is a purified or partially purified RNA polymerase available to stimulate transcription from the promoter. Promoters and polymerases considered to be particularly suitable are the SP6, T7 and T3 combinations, these are generally preferred as they are commonly used in the art and the RNA polymerases are, therefore, the most readily available.

However, the nature of the promoter used is not believed to be critical to practicing the invention and other promoters and polymerases may be employed in accordance herewith. For example, virtually any phage polymerase and promoter (Zillig et al. 1992), as exemplified by those derived from K11 phage (Klement et al., 1990), *B. subtilis* SP01 phage (Romeo et al. 1986), *B. subtilis* phage phi 29 (Pulido et al., 1986), and N4 phage may be used. Virtually any bacterial promoter may also be used, such as any *E. coli* or *Bacillus subtilis* promoter and polymerase combination.

Viral promoters include the SV40 early and late promoters from simian virus 40 (Ernoult-Lange et al., (1984), the Baculovirus polyhedron enhancer/promoter element, Herpes Simplex Virus thymidine kinase (HSV tk), the 35S promoter from Cauliflower Mosaic Virus (CMV), the Rous sarcoma long-terminal repeat (LTR) sequence, and various retroviral promoters. Plant and animal promoters may include promoter sequences from significantly expressed genes such as the α-tubulin gene and various zein genes in plants and immunoglobulin and hormone genes in animals. Suitable promoting sequences for yeast vectors include the promoters for 3-phosphoglycerate kinase and other glycolytic enzymes.

In vivo, additional promoter-type elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences interact with transcriptional machinery in fundamentally the same way.

In certain practical molecular biological embodiments such as in vitro transcription, enhancer units will not often be required as the promoters used are able to function effectively upon the addition of the corresponding RNA polymerase. However, there is no reason why an enhancer element should not be added to a multiple promoter vector in accordance with the present invention if desired. The addition of an enhancer element is most likely when it is combined with the promoter element in close proximity, or even overlaps with the promoter, one such example is the Baculovirus polyhedron enhancer/promoter.

Two, three or more of any of the promoters listed above, or any other promoter or promoter/enhancer elements as desired, may be employed in tandem in the vectors and plasmids of the present invention. When it is known that only transcription using two polymerases will be needed for a particular study, such as in a collaborative venture between two laboratories, the use of a two promoter plasmid may be advantageous due to the ease of construction.

The basic procedures for creating a plasmid for use in in vitro transcription reactions may involve any of several suitable general strategies. For example, the simplest strategy for creating a plasmid vector with multiple promoters for use in in vitro transcription reactions is to ligate into a plasmid a double stranded oligonucleotide that contains the multiple promoter sequences but which destroys the plasmid's unique cloning site(s) that was (were) used, thereby providing a selection scheme for the recombinant plasmid. This method requires the synthesis of two oligos that will hybridize together and create two to four base overhand extensions at both ends that will hybridize and be ligated to appropriately restricted plasmid DNA, but which cannot be recur with the original restriction enzyme(s) once ligated into the vector.

In this straightforward method, the oligos will also contain the promoter sequences that are to be cloned. The distance between the multiple promoters is not critical. Larger spacing between promoters will result in larger amounts of spacer sequence in the transcription product when transcribed by any multiple promoter other than the promoter proximal to the multiple cloning site. Typically the spacing between the promoters will be several bases except in situations where restriction sites are introduced between promoters. In this case, specific sequences may be cloned between promoters resulting in larger spaces between the promoters. The unique cloning site(s) used should be at either 5' end of the multiple cloning site and the promoters directed towards the other unique cloning sites. Once the ligation reaction is done and the DNA is transformed into *Escherichia coli*, the recombinant plasmids that contain the promoter sequences can be identified by the lack of restriction by the original restriction enzyme(s) used.

A method to ligate a double stranded oligo into a restricted plasmid but destroy the original restriction site is illustrated by the following. This method can be easily adapted for use with any restriction site, but for the following example the restriction site for the enzyme Eco R1 is used:

```
- N N G        A A T T C N N-    -N N G        A A T T T N N-
-N N C T T A A          G N N-   -N N C T T A A        A N N-

"Vector"      "Vector"          "Vector"       "Oligo"
```

The left side shows the correct, recuttable site, the right side shows the ligatable, but uncuttable site. The recognition site for Eco R1 is "GAATTC". The bases in italics are the bases that prevent the enzyme, Eco R1, from recutting the site.

Alternatively, another method to clone a DNA promoter sequence is by general restriction enzyme cleavage and DNA Ligation of one segment, the promoter sequence, into a plasmid vector. The methods for restriction enzyme cleavage and DNA Ligation are described in detail in Sambrook, et al., 1989, incorporated herein by reference. Once the DNAs are ligated, transformed, and purified from a single colony, the insertion of the promoter sequence desired may be verified by many methods, including restriction digestion, PCR amplification, and DNA sequencing, as will be known to those of skill in the art in light of the present disclosure.

A third strategy is to generate DNA sequencing containing promoters by PCR. The PCR primers can contain restriction enzyme sites allowing the generation of promoter containing DNA fragments with single stranded overhang extensions, most preferable 4 base, that can be ligated into vector DNA to add a promoter sequence to a vector. This procedure can be repeated sequentially to add additional promoter sequences. This PCR strategy can also be used be generate linear DNA containing multiple promoters and a sequence to be transcribed downstream of the promoter. This method allows transcription competent DNA to be generated without cloning.

One particular scheme for constructing a plasmid with two promoters is set forth in Example III. The promoters used may be SP6 and T7, SP6 and T3 or T3 and T7, or may of course be any of combination of phage, virus, bacterial, plant or animal promoters, chosen according to the intended function of the resultant plasmid.

One particular example of a novel plasmid which contains three promoters is that termed pTRIPLEscript™, as described in Example VI. Another vector with three tandem promoters is that described in Example IV which contains the T7, K11, and SP6 promoters. The starting plasmid for this construction is pSP65, which contains a functional SP6 promoter, to which T7 and K11 promoters are added by ligating in a synthetic oligonucleotide cassette.

Multiple promoter vectors and plasmids also fall within the scope of invention. These may contain generally any number of promoters greater than one, i.e., at least two, so long as the resultant vector or plasmid is functionally operational, i.e., capable of producing RNA transcripts. Any combination of phage, virus, bacterial, plant or animal promoters may also be used in multiple promoter vectors, as desired. Particular examples are contemplated which contain promoters for in vitro transcription and a promoter suitable for use in in vivo transcription. For example, the construction of a plasmid which contains the three commonly-used phage promoters, SP6, T7 and T3, in addition to an SV40 promoter for in vivo transcription is described in Example V. A convenient starting material for such constructs would be the plasmid pTRIPLEscript, into which would be inserted the SV40 promoter or Baculovirus polyhedron enhancer/promoter in the same orientation as the three phage promoters. Such multiple promoter vectors could be used as "shuttle vectors" which can be used both in vitro, for in vitro transcription reactions, and also in vivo in eukaryotic or procaryotic host cells in addition to the E. coli host in which it is propagated.

The vectors and plasmids of the present invention will have at least a single restriction enzyme site into which the exogenous DNA which is to be transcribed will be inserted. More preferably they will contain a number of restriction sites, i.e., a multiple cloning site, allowing manipulation using a variety of different enzymes. The number and type of such restriction sites is not crucial to the invention and virtually any number and specific type may be employed. An extremely large number of restriction enzyme sites have now been documented (e.g., see Sambrook et al., 1989, incorporated herein by reference), virtually any of which would be suitable for use herewith. Commercial constructs which may be employed in this regard are those of Bluescript and superlinker vectors (Heusterspreute et al., 1985; Brosius, 1992; Alting-Mecs & Short, 1989).

It is important to note that the present invention is by no means limited to having one or more restriction sites distal to all of the promoters, rather, they may be present between any two or more of the promoters. Using this type of construct would allow different sequences to be cloned at different positions in the vector, e.g., two different sequences at two different positions, three different sequences at three different positions, etc. In such embodiments, transcription with one polymerase would allow the transcription of just one of the sequences. Depending on the particular construction employed, transcription with a distinct polymerase may result in the transcription of a distinct sequence or may promote the synthesis of a single transcript containing two or more sequences, i.e., a polytranscript.

A particularly preferred novel plasmid vector has been developed which contains triple promoters, allowing a single vector to be employed in connection with any of the commonly-used phage polymerases to generate RNA transcripts. This particular new vector is a plasmid cloning vector termed pTRIPLEscript™ which is commercially available from Ambion (Ambion, Austin, Tex.).

pTRIPLEscript™ contains the SP6, T7, and T3 phage promoters in tandem and allows the use of any of the three phage promoters to transcribe cloned DNA. This vector efficiently synthesizes in vitro transcripts from all three promoters under both conditions of limiting nucleotide (high specific activity probe synthesis) and saturating nucleotide concentrations (unlabeled mRNA synthesis). Furthermore, closely spacing these three promoters in the vector did not result in crosstalk, i.e., initiation at inappropriate promoters, which could affect translation studies.

The utility of multiple promoter plasmid cloning vectors such as pTRIPLEscript™ is particularly highlighted by the inventors finding of a situation where a low level of premature termination occurred using SP6 RNA polymerase, but did not when using T7 or T3 RNA polymerase. Subcloning and transcribing with T7 RNA polymerase gave nothing but full length transcripts. These kind of situations clearly show the distinct advantages provided by transcription vectors which contain multiple promoters, and demonstrate the value of vectors such as pTRIPLEscript™.

The present invention is of course not limited in its scope to the particular vector "pTRIPLEscript™". Rather, a variety of vectors and plasmids with two, three or multiple, uni-directional promoters may now be created in light of the new ideas disclosed herein. The vectors may be generally designed to function in any molecular biological application and may contain other elements, such as, for example, genes facilitating selection or detection, such as antibiotic resistance genes; elements which allow propagation in both in prokaryotes and eukaryotes, such as E. coli/yeast shuttle vectors; vectors which promote integration or maintenance in mammalian cell, and the like.

Naturally, the recombinant DNA insert or 'transgene' may be virtually any type of exogenous DNA segment or gene and will be dependent on the intended function of the RNA produced by the in vitro synthetic reaction. The DNA insert may be any coding or non-coding DNA to which one wishes to generate an RNA probe, for use in, e.g., Northern or Southern blotting, FISH embodiments, RNase protection assays, or further cloning, sub-cloning or mutagenesis and the like.

The DNA insert may also encode an entire gene, a functional protein domain, or any polypeptide, peptide, antigenic fragment or epitopic core region, or may encode the antisense version of any of the above. In vitro transcription may then be used to synthesize synthetic mRNAs, for use either in in vitro translation to produce proteins or peptides or in antisense technology to inhibit the effective transcription or translation of a given gene or construct. A single recombinant insert may be used to encode two or more distinct protein sequences, which may later be separated at the RNA stage or the protein stage. The vectors may also be constructed so that different RNA polymerases promote transcription of different DNA segments inserted into restriction sites between the promoters.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

PROMOTER AND POLYMERASE COMBINATIONS

A variety of promoters may be employed in connection with the present invention. The general requirement is that transcription from the chosen promoter should be stimulated in vitro by a purified or partially purified RNA polymerase, preferably one which uniquely recognizes the particular promoter. Those promoters and polymerases considered to be particularly suitable are the SP6, T7 and T3 combinations.

As is known to those working in this field, there is variability in size and base composition for each phage promoter. The sequences of typical SP6, T7 and T3 promoters are represented below and have been chosen by the inventors as sequences commonly used in vector construction. These sequences form integral parts of SEQ ID NO:2, as specifically marked on FIG. 1A.

Figure 1A:
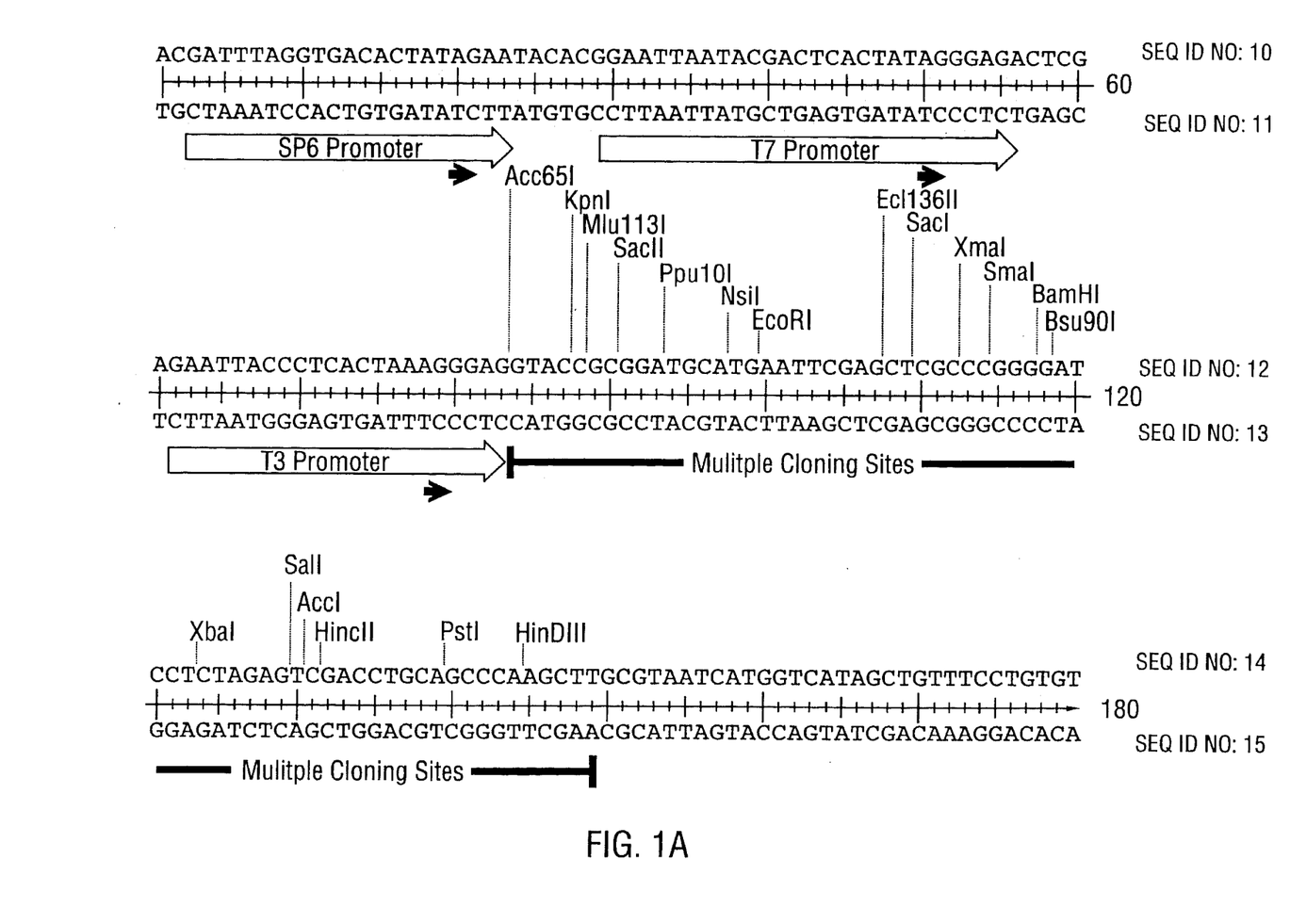
FIG. 1A. The new sequence. All sites shown are unique, cloning sites. The darkened triangle signifies the transcription start site for the respective promoter. The top line sequence is represented by SEQ ID NO:1 and the bottom line sequence is represented by SEQ ID NO:2.

| | |
|---|---|
| SP6 | nucleotides 4–23 of SEQ ID NO:2 |
| T7 | nucleotides 34–56 of SEQ ID NO:2 |
| T3 | nucleotides 63–82 of SEQ ID NO:2 |

SP6 polymerase is derived from the *S. typhimurium* phage SP6, and the T7 and T3 polymerases are derived from the *E. coli* phages T7 and T3. All of these are available commercially, for example, from Ambion, Promega, Pharmacia, and may be purified according to the methods set forth in the literature, for example, Tabor et al. (1985); Morris et al. (1986); and Butler et al., (1982), each incorporated herein by reference.

However, the present invention is not limited to the use of the SP6, T3 and T3 promoters and polymerases and many other combinations are envisioned to be of use in accordance herewith. For example, other phage polymerases have been isolated or have been purified from various sources and are encompassed by the present invention. These include, but are not limited to, promoter and polymerase combinations such as those derived from N4 phage, the ghl (Pseudomonas host) promoter, K11 phage (Klement et al., 1990), *B. subtilis* SP01 phage (Romeo et al. 1986), and even the *B. subtilis* phage phi 29 promoter (Pulido et al., 1986). Each of the foregoing references are incorporated herein by reference.

Other polymerases, and the promoters they recognize, which may be used in vectors of the invention include, for example, *E. coli* RNA polymerase with various promoters (Jovanovich et al., 1989); *Bacillus subtilis* RNA polymerases with various sigma-like subunits and related promoters; other suitably specific bacteriophage polymerases and their promoters (Zillig et al. 1992); the SV40 late promoter from simian virus 40 (Ernoult-Lange et al., (1984); and various plant and animal derived RNA polymerases and their promoters.

EXAMPLE II

MULTIPLE CLONING SITES AND VECTORS

Figure 1B:
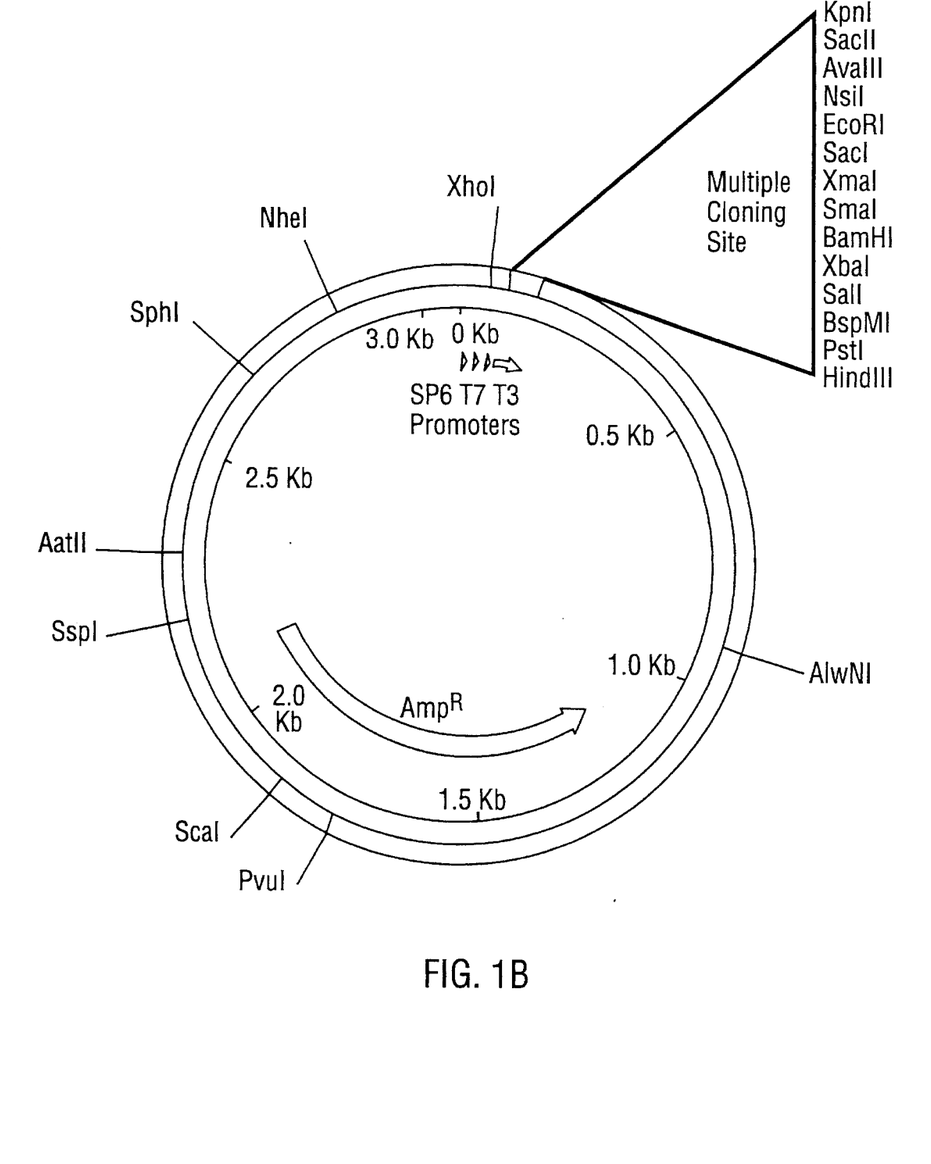
FIG. 1B. The plasmid termed pTRIPLEscript™.

Naturally, at least a single restriction enzyme site must be present in the vectors of the present invention so that the exogenous DNA which is to be transcribed can be inserted. However, it is generally preferred that a number of restriction sites, i.e., a multiple cloning site, be used. One example of such a construction is presented in FIG. 1. However, this is by no means limiting and other multiple cloning sites may be employed, such as, for example, Bluescript and superlinker vectors (Heustersprente et al., 1985; Brosius, 1992; Alting-Mecs & Short, 1989).

Furthermore, the addition of restriction sites is not limited to being distal to all the promoters and they may be present between promoters. This would allow two different sequences to be cloned at two different positions in the vector. Transcription with one phage polymerase would result in the transcription of just one of the sequences. Transcription with another polymerase would result in the synthesis of a single transcript containing both sequences.

As to the particular vectors themselves, a variety of plasmid vectors with multiple, uni-directional promoters may be constructed in light of the novel concepts enabled by the present inventors. The vector may be generally designed to function in any molecular biological application, and the construction of the remaining portion of the vector is not critical to the functioning of the transcription region under the control of the multiple promoters. Vectors which may be used in conjunction with the present invention include a variety of plasmids which contain genes facilitating selection, for example, genes contributing antibiotic resistance; bacteriophage vectors such as lambda or related phages; shuttle vectors designed to be propagated both in prokaryotes and eukaryotes, such as *E. coli* /yeast vectors; vectors which produce fusion proteins or which fuse the cloned DNA with regions of the vector which control expression; vectors capable of transforming mammalian cells and which might either integrate into the genome or be maintained or replicated extrachromosomally; and viral vectors for use with mammalian cells.

The recombinant DNA insert used in connection with the vectors of the invention may be of virtually any type. The DNA employed will, of course, be dependent on the intended function of the RNA produced by the in vitro synthetic reaction. As in vitro transcription is used to synthesize RNA probes, e.g. for use in Northern and Southern blotting, in situ hybridization and ribonuclease protection assays, the DNA insert may be any coding or non-coding DNA to which one wishes to generate a probe for use in screening, further cloning, manipulation or other analyses. In vitro transcription is also used to synthesize synthetic mRNAs for use, e.g., in in vitro translation, microinjection and antisense technology. In these embodiments, the DNA inserts may encode entire genes; functional protein domains;

polypeptides and peptides; antigenic fragments; or may encode the complement (antisense version) of any such sequence.

EXAMPLE III

VECTORS WITH TWO PROMOTERS IN TANDEM

One example of a vector with two tandem promoters is one which contains a T7 and SP6 promoter directed towards a unique cloning site. Many ways are available to make such a vector, and one representative example of a construction scheme for such a plasmid vector is described as follows.

The starting plasmid is pSP65 which contains a functional SP6 promoter. A T7 promoter is added by ligating in a synthetic oligonucleotide cassette. Two oligonucleotides were designed that would hybridize together but leave 5' and 3' overhangs that would ligate to EcoRI and Sac I digested DNA, respectively. The sequence of the top strand is shown below and represents SEQ ID NO:5:

AATTA ATACG ACTCA CTATA GGGAG ACTCG AGGAG CT

The sequence of the bottom nucleotide is shown below and represents SEQ ID NO:6:

CCTCG AGTCT CCCTA TAG TG AGTCG TATT

The oligonucleotides were designed such that the EcoRI site would be destroyed and the SacI site restored when it was ligated to EcoRI and SacI digested pSP65 DNA. The oligo would add a T7 promoter to the plasmid, which in this example is pSP65, which would result in two tandem promoters directed towards the multiple cloning site, i.e. T7 and SP6 promoters. The oligo would also add an Xho I site between the two promoters for screening and or cloning purposes, as described in Example VI.

The methods of cloning, purifying, and transcribing such an example plasmid vector are described in detail in the Materials and Methods section of Example VI. Such a two promoter vector would be simpler to construct then triple promoter vectors, and is envisioned for use in any situations where it is not particularly desirable to have three promoters in the same vector.

EXAMPLE IV

VECTORS WITH THREE PROMOTERS IN TANDEM

One example of a vector with three tandem promoters is one which contains a T7, K11, and SP6 promoter directed towards a unique cloning site. As with the double promoter constructs, there are many ways to construct such a vector, and one representative example of a construction scheme is described as follows.

The starting plasmid is pSP65 which contains a functional SP6 promoter. T7 and K11 promoters are added by ligating in a synthetic oligonucleotide cassette. Two oligonucleotides were designed that would hybridize together but leave 5' and 3' overhangs that would ligate to EcoRI and Sac I digested DNA, respectively. The sequence of the top strand is shown below and represents SEQ ID NO:7:

| AATTA | ATACG | ACTCA | CTATA | GGGAG | ACTCG | AGAAT | TAGGG | CACAC |
| TATAG | GGAAC | GAGCT | | | | | | |

The sequence of the bottom strand nucleotide is shown below and represents SEQ ID NO:8:

| CGTTC | CCTAT | AGTGT | GCCCT | AATTC | TCGAG | TCTCC | CTATA | GTGAG |
| TCGTA | TT | | | | | | | |

The oligonucleotides were designed such that the EcoRI site would be destroyed and the SacI site restored when it was ligated to EcoRI and SacI digested pSP65 DNA. The oligo would add a T7 and K11 promoter to the plasmid, which in this example is pSP65, that would result in three tandem promoters directed towards the multiple cloning site, i.e. T7, K11, and SP6 promoters. The oligo would also add an Xho I site between the two promoters for screening and or cloning purposes, as described in Example VI. The methods of cloning, purifying, and transcribing such an example plasmid vector are described in detail in the Materials and Methods section of Example VI.

EXAMPLE V

VECTORS WITH MULTIPLE PROMOTERS IN TANDEM

A particular example of a vector with multiple promoters is one which contains an SV40 promoter or Baculovirus polyhedron enhancer/promoter for in vivo transcription in addition to three phage promoters for in vitro transcription. The following sequence could be inserted into the pTRIPLEscript vector, constructed as described herein (Example VI), that already contains three phage promoters for T7, T3, and SP6 RNA polymerases.

The following SV40 promoter sequence could be inserted as a PCR product into the Eco RI site of pTRIPLEscript directed in the same orientation as the three phage promoters. The plasmid purification and transcription conditions would be the same as that for pTRIPLEscript, and described in the Materials and Methods section of Example VI. The sequence shown below is the top strand, this is as set forth by Ernoult-Lange et al. (1984), and represents SEQ ID NO:9:

| TAGAGGATCG | ATCCTGACTA | ATTGAGATGC | ATGCTTTGCA | TACTTCTGCC |
| TGCTGGGGAG | CCTGGGGACT | TTCCACACCT | GGTTGCTGAC | TAATTGAGAT |

-continued

| GCATGCTTTG | CATACTTCTG | CCTGCTGGGG | AGCCTGGGGA | CTTTCCACAC |
| CCTAACTGAC | ACACATTCCA | CAGCTGGTTC | TTTCCGCCTC | AGAAGGTACC |
| TAACCAAGTT | CCTCTTTCAG | AGGTTATTTC | AGGGATCCTA | TTCCAGAAGA |

Such a multiple promoter vector could be a "shuttle vector" which can be used both in vitro for in vitro transcription reactions, but also could be used in vivo in eukaryotic or procaryotic host cells in addition to the *E. coli* host in which it is propagated.

EXAMPLE VI

DESIGN AND CONSTRUCTION OF pTRIPLEscript™

A. Materials and Methods

1. Vectors and Strains

The plasmid vector pSP65 was purchased from Promega, Madison, Wis. The *Escherichia coli* strain, DH5α, was purchased from BRL, Gaithersburg, Md. *E. coli* was grown in 2xYT containing 100 µg/ml carbenicillin (Sigma, St. Louis, Mo.).

2. Design and Construction of the Plasmid Vector, pTRIPLEscript™

Two oligonucleotides were designed that would hybridize together but leave 5' and 3' overhangs that would ligate to EcoRI and SacI digested DNA, respectively. The sequence of the top strand oligonucleotide is shown below and represents SEQ ID NO:3

| AATTA | ATACG | ACTCA | CTATA | GGGAG | ACTCG | AGAAT | TACCC | TCACT | AAAGG |
| GAGGTA | CCGCG | GATGC | ATGAA | TTCGA | GCT | | | | |

The sequence of the bottom strand nucleotide is shown below and represents SEQ ID NO: 4.

| CGAAT | TCATG | CATCC | GCGGT | ACCTCC | CTTTA | GTGAG | GGTAA | TTCTC | GAGTC |
| TCCCT | ATAGT | GAGTC | GTATT | | | | | | |

The oligonucleotides were designed such that the EcoRI site would be destroyed and the SacI site restored when it was ligated to EcoRI and SacI digested pSP65 DNA. In addition to inserting T3 and T7 RNA polymerase promoter sequences, the oligonucleotide also inserted three unique restriction sites that left 3' overhangs (KpnI, SacII, and NsiI) just proximal to a new EcoRI site (FIG. 1). The extra 3' overhang restriction sites were included to allow for use of the exo-deletion sequencing method. The inventors also inserted a unique XhoI site between the T3 and T7 promoters to facilitate screening for recombinants. The resulting sequence of the new construct, pTRIPLEscript™, is shown in FIG. 1. The sequence from bases 31 to 109 (of SEQ ID NO:1) correspond to the double-stranded oligonucleotides.

B. Results and Discussion

The 11 promoters for bacteriophage T3 and 17 promoters for bacteriophage T7 RNA polymerase have been well characterized and their strengths compared. The T3 and T7 promoters have been divided into three groups, class II, class III, and replication promoters, with the class III promoters being the strongest (Dunn et al., 1983; Sengupta et al., 1989). From each of these the inventors chose a class III promoter sequence that was shown to be as strong or stronger in vitro than any other. For the T7 promoter, the φ10 sequence was chosen and for T3 the sequence for the promoter at 55.0 map units was chosen (Dunn et al., 1983; Sengupta et al., 1989).

On the other hand, there have only been four bacteriophage SP6 RNA polymerase promoters that have been cloned and sequenced, and their relative strengths have not been determined (Melton et al., 1984; Brown et al., 1986). However, the sequences of the four promoters are identical from the +3 nt to the −17 nt (inclusive), with one exception: at the −10 nt. position two of the promoters have a G, the other two have a T. The transcription plasmids pSP64 and pSP65, developed by Melton et al. (1984) have a T at this position. The inventors decided to simplify the construction of pTRIPLEscript™ by adopting pSP65 as the starting backbone, since its SP6 promoter has been used extensively and is known to function very well in vitro. Furthermore, the relative strength of the only other known sequence for an SP6 promoter has not been reported.

A double-stranded oligonucleotide that contained the chosen T3 and T7 promoter sequences was ligated to EcoRI and SacI digested pSP65 and transformed into *Escherichia coli* strain DH5α. The recombinant clones were found by digesting the miniprep plasmids with XhoI; nonrecombinants would not be cut with XhoI. Three independent clones were sequenced throughout the promoter and multiple cloning regions in both directions and found to agree completely. The sequence of this region is shown in FIG. 1. One of the three clones was chosen arbitrarily to be designated as "pTRIPLEscript™", and was used from this point onward.

After analyzing the sequence data and comparing it to the published sequence for the parent plasmid (pSP65) we found that there was a base deleted in a region that should not have been affected. The deleted base is a G residue that should be between 150 and 151 nt. in the pTRIPLEscript™ sequence and is found at position 62 in the pSP65 sequence, taken from GENBANK release no. 76 using the locus name, CVPSP65. The inventors then sequenced their original source for pSP65 and found the same G residue deleted. It is believed, therefore, that there may be an error in the sequence for pSP65 and perhaps pSP64. However, the deleted base is not believed to have any adverse effects, as is shown by the advantageous functions of the vectors disclosed herein.

EXAMPLE VII

THE EFFECT OF TANDEM PHAGE PROMOTERS ON IN VITRO TRANSCRIPTION REACTIONS

A. Materials and Methods

1. Transcription Reactions

The synthesis of high specific activity transcripts normally utilizes a subsaturating concentration of one nucleotide, e.g., [$\alpha^{32}$P]-UTP. The inventors used 50 µCi (at 800 Ci/mmol) per 20 µl reaction, which is equivalent to a concentration of 3 µM UTP. 10 µM cold UTP was added to make a total UTP concentration of 13 µM. The other three nucleotides were at a concentration of 0.5 mM. 10 units of RNA polymerase and 0.5 µg of linearized template plasmid were used per reaction. One unit of activity is defined as the amount of RNA polymerase that will incorporate 1 nmole of [$\alpha^{32}$P]-UTP into acid precipitable material in 60' at 37° C. using 1 µg of pTRIPLEscript-actin linearized with Hind III. The transcript made is approximately 300 nt. The specific activity of the SP6 RNA Polymerase used is $3\times10^5$ U/mg, the T3 used is $1\times10^5$ U/mg, and the T7 used is $1.7\times10^5$ U/mg.

The transcription reactions done with saturating amounts of RNA polymerase to template plasmid were done with all four nucleotides at a concentration of 0.5 mM and up to 100 units of RNA polymerase per 20 µl reaction. The other components were held the same. The radioactive nucleotide used was Amersham's [$\alpha^{32}$P]-UTP, 800 Ci/mmol. Transcription products were analyzed on an 8M urea, 5% polyacrylamide gel and subsequently dried down on Whatman 3MM chromatography paper prior to autoradiography.

2. Densitometry of Autoradiograms

Autoradiograms of the dried down gels were scanned into a Macintosh™ IIVX computer using the Apple Color OneScanner™. The unaltered images were saved as TIFF files and opened in Wayne Rashand's Image Program. The densitometry functions were carried out using the gel plot macro. The densities of each hand were transformed to cpm by the use of a standard curve.

B. Results and Discussion

The inventors tested the pTRIPLEscript™ transcription vector under two different transcription conditions, with each of the three RNA polymerases, and with a variety of inserts. The two most commonly used transcription conditions are making low mass amounts of transcript under subsaturating nucleotide concentrations and making large mass amounts of transcript under saturating nucleotide and polymerase concentrations.

Figure 2:
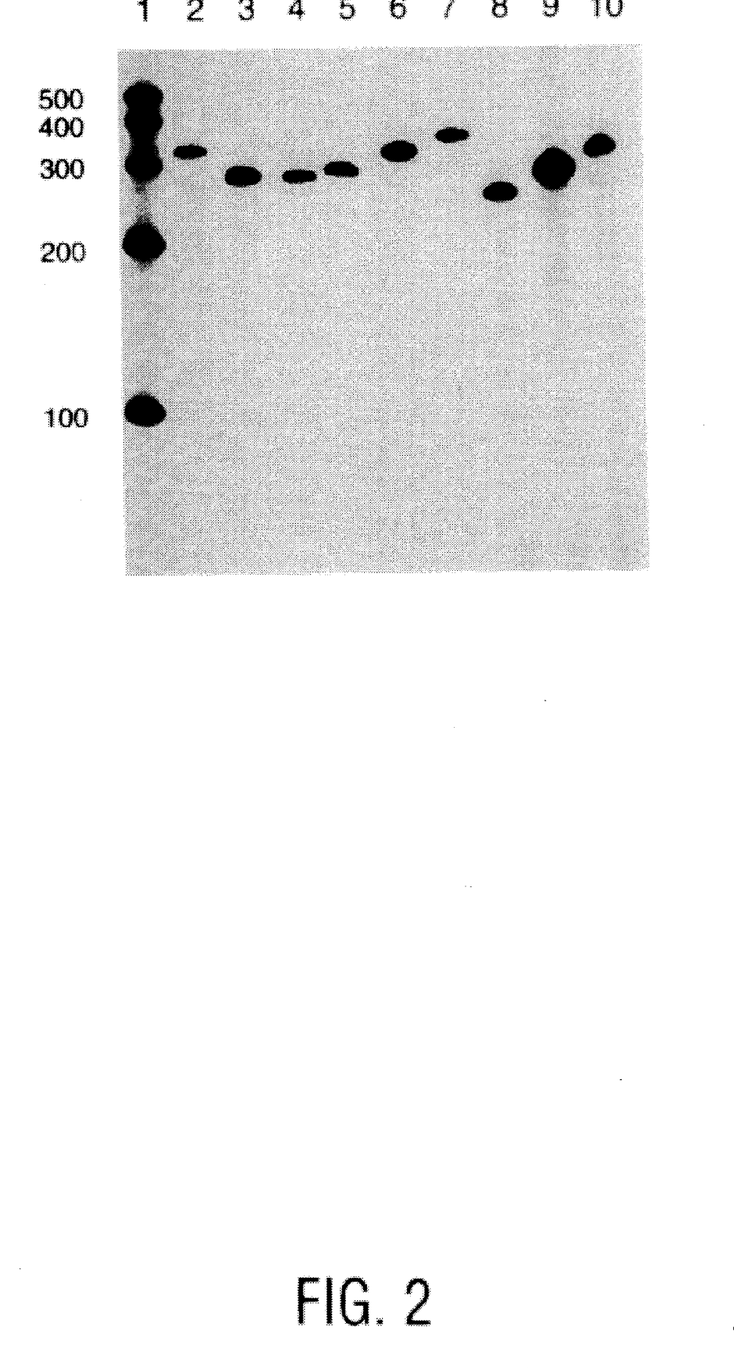
FIG. 2. Transcription of pTRIPLEscript vs. conventional transcription vectors. All transcription reactions were done with 10 units of RNA polymerase, 0.5 μg of linearized template plasmid, and 13 μM UTP. Lane 1 is the RNA molecular mass markers of length 100, 200, 300, 400, and 500 nt. Lanes 2, 3, and 4 are conventional transcription vectors containing a 250 nt. insert of the mouse β-actin gene using T3, T7, and SP6 RNA polymerases, respectively. Lanes 5, 6, and 7 are pTRIPLEscript containing the same β-actin insert and using T3, T7, and SP6 RNA polymerase, respectively. Lanes 8, 9, and 10 are pTRIPLEscript linearized with Pvu II using T3, T7, and SP6 RNA polymerases.

FIG. 2 shows the results of transcribing linearized pTRIPLEscript™ with (lanes 5, 6, and 7) or without (lanes 8, 9, and 10) a 250 bp mouse β-actin insert using each of the three polymerases. Also shown as a reference are the mouse β-actin transcripts made from vectors that contain a single promoter (lanes 2, 3 and 4). The pTRIPLEscript™ without the β-actin insert was cut with Pvu II which cuts once 250–300 nt downstream of the tandem promoters. The conditions were for labeling the RNA transcript to high specific activity (with a total concentration of UTP equal to 13 µM). Because the three RNA polymerases start at sites that differ by 28–30 nt, the inventors were able to resolve each of the transcription products on a 5% polyacrylamide, 8M urea gel. A particularly important result is that there is no detectable "crosstalk" (i.e., use of a wrong promoter by a polymerase) with any of the three RNA polymerases. The level of detection using densitometry of the longest exposed autoradiograph was ≦1%. The densitometry was conducted using a flatbed scanner coupled with Wayne Rasband's Image program for the Macintosh™, as described in the Materials and Methods section.

In the transcription conditions described above, using 10 U of RNA polymerase and 0.5 µg of a 3662 bp plasmid template, the template is present at a concentration of 0.21 pmoles per 20 µl reaction. With a specific activity of $3\times10^5$ U/mg, the SP6 used is present at a concentration of 0.34 pmoles per 20 µl reaction. The T3 and T7 enzymes used have specific activity of $1.0\times10^5$ U/mg and $1.7\times10^5$ U/mg, respectively, which results in concentrations of 0.60 pmoles and 1.0 pmoles per 20 µl reaction, respectively. Therefore, these transcription conditions use a roughly 1:2 molar ratio of template to enzyme.

The inventors next tested pTRIPLEscript™ in transcription conditions designed to make larger mass amounts of a transcript, which necessitates using larger molar excesses of RNA polymerase to template. For these reactions 80 U of each RNA polymerase and 0.5 µg of template plasmid were used, which is a 16 fold excess of polymerase. FIG. 3 shows a comparison of the two transcription reaction conditions using pTRIPLEscript™ with the 589 bp sense strand of rabbit β-globin. Lanes 2–4 are limiting nucleotide conditions, i.e. 13 µM UTP, and Lanes 6–8 are saturating nucleotide, i.e. 0.5 µM each, and 80 U RNA polymerase reaction.

Figure 3A:
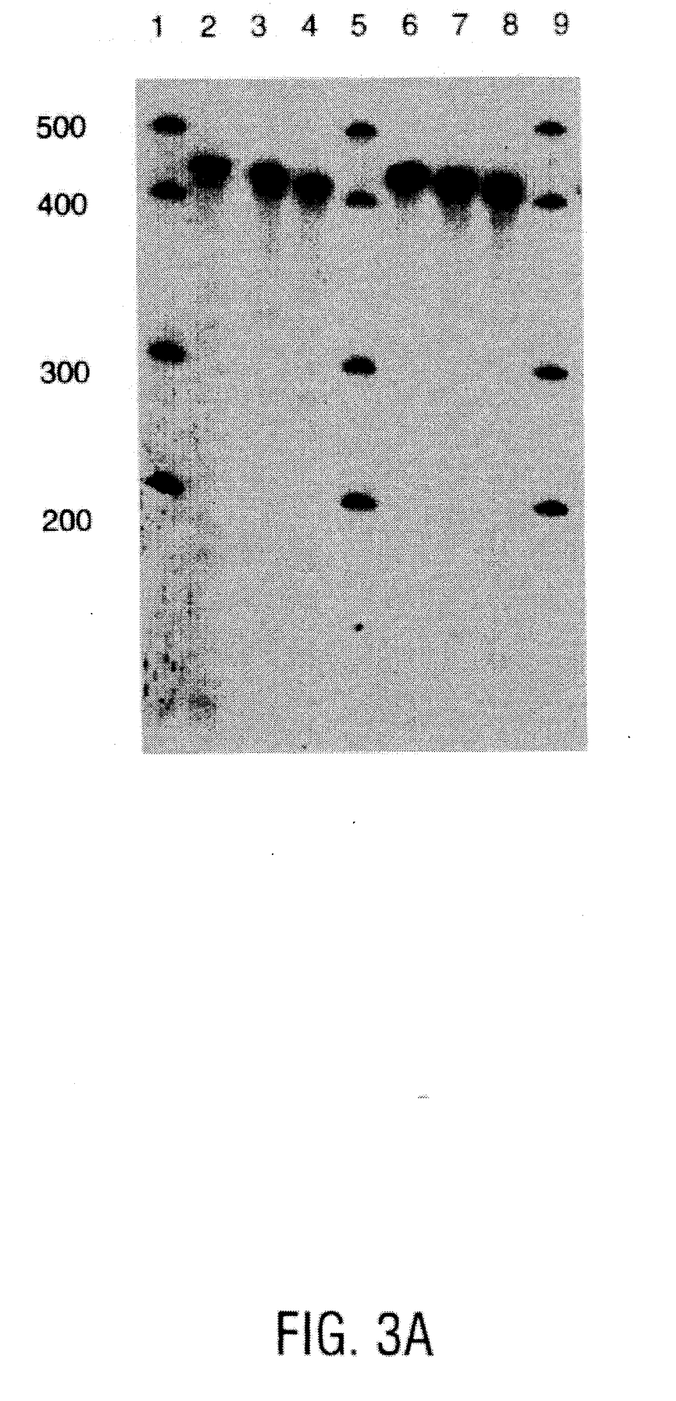
FIG. 3A is 30 minute exposure with an intensifying screen.
Figure 3B:
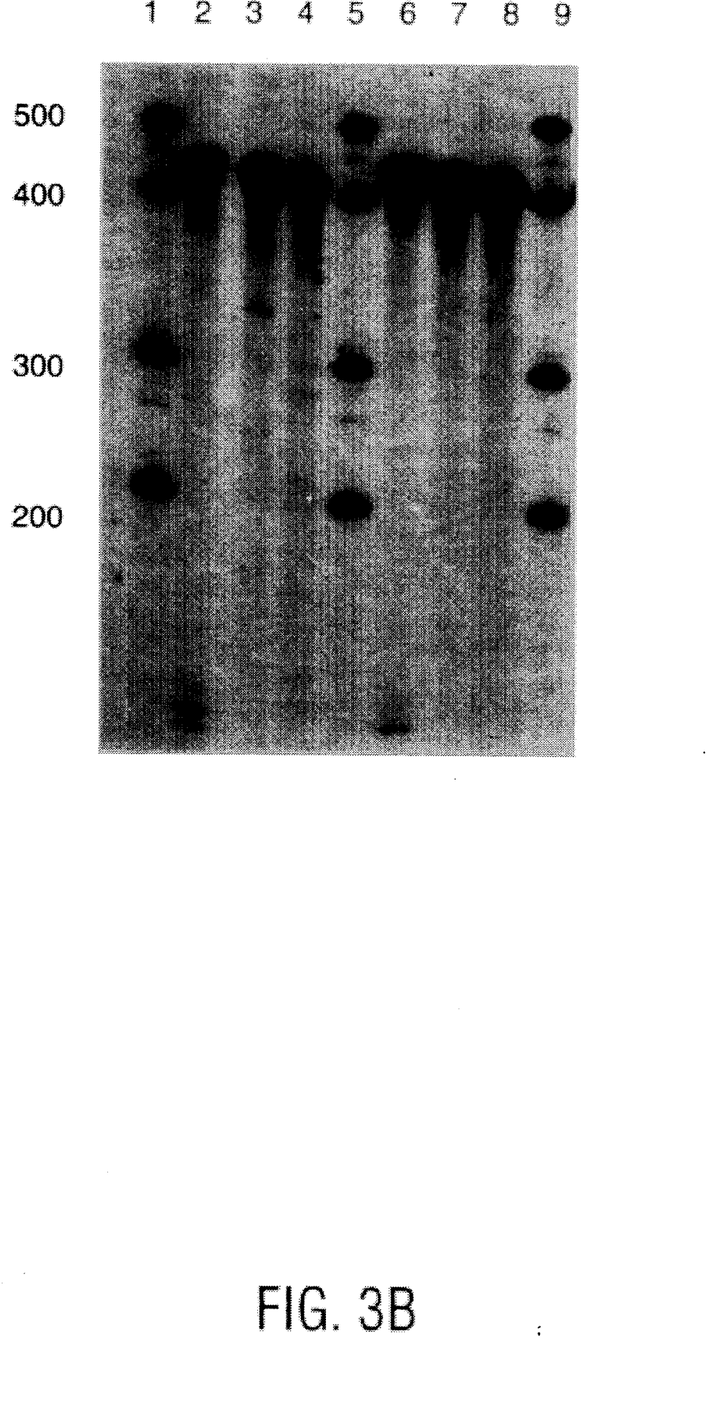
FIG. 3B is a 4-fold longer exposure.

Here again it is important to note that in panel A (30' exp) there is no apparent crosstalk in either transcription condition. Furthermore, the 4× longer exposure shown in panel B demonstrates a mild case of "sequence-dependent" premature termination that is also RNA polymerase dependent. It is only present in the SP6 RNA polymerase reactions and is somewhat decreased in the saturating nucleotide transaction conditions versus the limiting nucleotide transaction conditions (compare lanes 2 and 6).

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are chemically, functionally and/or structurally related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references, to the extent that they provide exemplary procedural or other details supplementary to those set forth herein, are specifically incorporated herein by reference.

Alting-Mecs, M. A., and J. M. Short, (1989). pBluescript II & gene mapping vectors. Nucl. Acids Res. 17, 9494-.

Brosius, J. (1992). Compilation of superlinker vectors. Meth. Enzym. 216, 469–483.

Brown, J. E., J. F. Klement, and W. T. McAllister (1986). Sequences of three promoters for the bacteriophage SP6 RNA polymerase. Nucl. Acids Res. 14, 3521–3526.

Butler, E. T., and M. J. Chamberlin, (1982). Bacteriophage SP6 - specific RNA Polymerase. J. Biol. Chem. 257, 5772–5778.

Dunn, J. J. and F. W. Studier (1983). Complete nucleotide sequence of bacteriophage T7 DNA and the locations of T7 genetic elements. J. Mol. Biol. 166, 477–535.

Ernoult-Lange, M., P. May, P. Moreau, and E. May, (1984). Simian virus 40 late promoter region able to initiate simian virus 40 early gene transcription in the absence of the simian virus 40 origin sequence.

Heusterspreute, M., V. H. Thi, S. Emery, S. Tournis-Gamble, N. Kennedy, and J. Davison, (1985). Vectors with restriction site banks. IV.pJRD184, a 3793-bp plasmid vector with 49 unique restriction sites (published erratum appears in Gene 1987;53(2–3):299–300) Gene 39, 299–304.

Jendriask et al., U.S. Pat. No. 4,766,072, 1988.

Klement, J. F., M. B. Moorefield, E. Jorgensen, J. E. Brown, S Risman, and W. T. McAllister, (1990). Discrimination between bacteriophage T3 and T7 promoters by the T3 and T7 RNA polymerases depends primarily upon a three base pair region located 10 to 12 base-pairs upstream from the start site. J. Mol. Biol. 215, 21–29.

Martin, C. T., and J. E. Coleman, (1987). Kinetic analysis of T7 RNA polymerase-promoter interactins with small synthetic promoters. Biochem. 26:2690–6.

Melton, D. A., P. A. Krieg, M. R. Rebagliati, T. Maniatis, K. Zinn, and M. R. Green (1984). Efficient in vitro synthesis of biologically active RNA and RNA hybridization probes from plasmids containing a bacteriophage SP6 promoter. Nucl. Acids Res. 12, 7035–7056.

Morris, C. E., K. F. Klement, and W. T. McAllister, (1986). Cloning and expression of the bacteriophage T3 RNA polymerase gene. Gene, 41, 193–200.

Sambrook et al. (1989). Molecular cloning: A laboratory manual. Cold Spring Harbor Laboratory. Cold Spring Harbor, N.Y.

Sengupta, D., D. Chakravarti, and U. Maitra (1989). Relative efficiency of utilization of promoter and termination sites by bacteriophage T3 RNA polymerase. J. Biol. Chem. 264, 14246–14255.

Tabor, S., and C. C. Richardson, (1985). A bacteriophage T7 RNA polymerase/promoter system for controlled exclusive expression of specific genes. Proc. Natl. Acad. Sci. 82, 1074–1078.

Zillig W., Palm, P., Langer, D., Klenk, H. P., Lanzendorfer, M., Hudopohl, U., and Hain, J. (1992) RNA polymerases and transcription in archaebacteria. Biochem. Soc. Symp. 58, 79–88.

---

What is claimed is:

1. A recombinant DNA for in vitro synthesis of RNA, comprising a site that accepts an RNA transcription unit, said site positioned downstream of a promoter region that includes at least two phage promoters in tandem that are recognized by distinct RNA polymerases.

2. The recombinant DNA of claim 1 wherein said promoter region has three phage promoters.

3. The recombinant DNA of claim 2 wherein the three phage promoters are SP6 phage promoter, T7 phage promoter and T3 promoter.

4. The recombinant DNA of claim 1 that includes at least two phage promoters selected from a group consisting of SP6, T3, T7, N4, K11, *B. subtilis* SP01 phage and *B. subtilis* phage phi 29 promoter.

5. The recombinant DNA of claim 2 wherein the promoter region includes the nucleotide sequence residues 1–79 of SEQ ID NO:1 or the complement thereof.

6. The recombinant DNA of claim 1 or claim 2 wherein the site includes two restriction enzyme cleavage sites.

7. The recombinant DNA of claim 1 wherein the site includes ten restriction enzyme cleavage sites.

8. The recombinant DNA of claim 1 wherein the site is a multiple cloning site that includes multiple restriction enzyme cleavage sites.

9. The recombinant DNA of claim 8 wherein the multiple cloning site includes the nucleotide sequence set forth by residues 80–150 of SEQ ID NO:1 or the complement thereof.

10. The recombinant DNA of claim 1 wherein an RNA transcription unit is inserted into the site, the unit being under the transcriptional control of the promoter region.

11. The recombinant DNA of claim 1 which is a plasmid.

12. A circular recombinant plasmid for the synthesis of RNA, comprising a promoter region that has three phage promoters in tandem each recognized by a distinct phage-encoded RNA polymerase, positioned upstream of and closely adjacent to a site that accepts an RNA transcription unit that is under transcriptional control of the phage promoters.

13. The recombinant plasmid of claim 12 wherein the three phage promoters are SP6 promoter, T7 promoter and T3 promoter.

14. The recombinant plasmid of claim 13 wherein the plasmid includes the nucleotide sequence set forth by SEQ ID NO:1 or SEQ ID NO:2.

15. The recombinant plasmid of claim 12 that is pTRIPLEscript™ shown in FIG. 1B.

16. The recombinant plasmid of claim 12 wherein an RNA transcription unit is inserted into said site, the unit being under the transcriptional control of the phage promoters.

17. A DNA segment for in vitro RNA synthesis, comprising a site that accepts an RNA transcription unit, the site being positioned downstream of a promoter region that includes at least two phage promoters in tandem recognized by distinct RNA polymerases, said promoters positioned to promote expression from such an RNA transcription unit.

18. A method for preparing an RNA transcript from a DNA sequence, comprising the steps of:

(a) preparing a recombinant vector comprising the recombinant DNA of claim 1;

(b) inserting a DNA sequence downstream of the promoters; and (c) contacting the vector containing the inserted DNA with a reaction mixture including an RNA polymerase that interacts with one of the promoters.

19. The method of claim 18 wherein the vector containing the inserted DNA is a circular plasmid vector that is linearized prior to contact with the reaction mixture.

20. The method of claim 18 wherein the promoter region has three phage promoters recognized by distinct RNA polymerases.

21. The method of claim 18 wherein said reaction mixture includes a phage-encoded RNA polymerase.

22. The method of claim 21 wherein the promoter region includes an SP6 promoter, a T7 promoter or a T3 promoter.

23. The method of claim 21 wherein the promoter region includes an SP6 promoter, a T7 promoter and a T3 promoter.

24. The method of claim 18 wherein the recombinant vector is the plasmid pTRIPLEscript™ shown in FIG. 1B.

25. The method of claim 18 wherein the reaction mixture includes a labeled nucleotide.

26. The method of claim 18 wherein the reaction mixture includes nucleotides at subsaturating or saturating concentrations.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:1:

```
ACGATTTAGG  TGACACTATA  GAATACACGG  AATTAATACG  ACTCACTATA  GGGAGACTCG      60
AGAATTACCC  TCACTAAAGG  GAGGTACCGC  GGATGCATGA  ATTCGAGCTC  GCCCGGGGAT     120
CCTCTAGAGT  CGACCTGCAG  CCCAAGCTTG  CGTAATCATG  GTCATAGCTG  TTTCCTGTGT     180
```

( 2 ) INFORMATION FOR SEQ ID NO:2:

( i ) SEQUENCE CHARACTERISTICS:
        ( A ) LENGTH: 180 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:2:

```
TGCTAAATCC  ACTGTGATAT  CTTATGTGCC  TTAATTATGC  TGAGTGATAT  CCCTCTGAGC      60
TCTTAATGGG  AGTGATTTCC  CTCCATGGCG  CCTACGTACT  TAAGCTCGAG  CGGGCCCCTA     120
GGAGATCTCA  GCTGGACGTC  GGGTTCGAAC  GCATTAGTAC  CAGTATCGAC  AAAGGACACA     180
```

( 2 ) INFORMATION FOR SEQ ID NO:3:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear     ( i x ) SEQUENCE DESCRIPTION: SEQ ID NO:3:

```
AATTAATACG  ACTCACTATA  GGGAGACTCG  AGAATTACCC  TCACTAAAGG  GAGGTACCGC      60
```

```
GGATGCATGA ATTCGAGCT                                                                                        79
```

( 2 ) INFORMATION FOR SEQ ID NO:4:

( i ) SEQUENCE CHARACTERISTICS:
        ( A ) LENGTH: 71 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:4:

```
CGAATTCATG CATCCGCGGT ACCTCCCTTT AGTGAGGGTA ATTCTCGAGT CTCCCTATAG    60

TGAGTCGTAT T                                                        71
```

( 2 ) INFORMATION FOR SEQ ID NO:5:

( i ) SEQUENCE CHARACTERISTICS:
        ( A ) LENGTH: 37 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:5:

```
AATTAATACG ACTCACTATA GGGAGACTCG AGGAGCT                             37
```

( 2 ) INFORMATION FOR SEQ ID NO:6:

( i ) SEQUENCE CHARACTERISTICS:
        ( A ) LENGTH: 29 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:6:

```
CCTCGAGTCT CCCTATAGTG AGTCGTATT                                     29
```

( 2 ) INFORMATION FOR SEQ ID NO:7:

( i ) SEQUENCE CHARACTERISTICS:
        ( A ) LENGTH: 60 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:7:

```
AATTAATACG ACTCACTATA GGGAGACTCG AGAATTAGGG CACACTATAG GGAACGAGCT    60
```

( 2 ) INFORMATION FOR SEQ ID NO:8:

( i ) SEQUENCE CHARACTERISTICS:
        ( A ) LENGTH: 52 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:8:

```
CGTTCCCTAT AGTGTGCCCT AATTCTCGAG TCTCCCTATA GTGAGTCGTA TT            52
```

( 2 ) INFORMATION FOR SEQ ID NO:9:

( i ) SEQUENCE CHARACTERISTICS:
        ( A ) LENGTH: 250 base pairs
        ( B ) TYPE: nucleic acids
        ( C ) STRANDEDNESS: single
        ( D ) TOPOLOGY: linear     ( i x ) SEQUENCE DESCRIPTION: SEQ ID NO:9:

```
TAGAGGATCG ATCCTGACTA ATTGAGATGC ATGCTTTGCA TACTTCTGCC TGCTGGGGAG    60

CCTGGGGACT TTCCACACCT GGTTGCTGAC TAATTGAGAT GCATGCTTTG CATACTTCTG   120

CCTGCTGGGG AGCCTGGGGA CTTTCCACAC CCTAACTGAC ACACATTCCA CAGCTGGTTC   180

TTTCCGCCTC AGAAGGTACC TAACCAAGTT CCTCTTTCAG AGGTTATTTC AGGGATCCTA   240

TTCCAGAAGA                                                         250
```